_US005755761A_

United States Patent [19]
Obino

[11] Patent Number: 5,755,761
[45] Date of Patent: May 26, 1998

[54] ATRIAL PACING CATHETER AND METHOD HAVING MULTIPLE ELECTRODES IN THE RIGHT ATRIUM AND CORONARY SINUS

[75] Inventor: Stanislao F. Obino, Minneapolis, Minn.

[73] Assignee: PharmaTarget, Inc., Plymouth, Minn.

[21] Appl. No.: 638,105

[22] Filed: Apr. 26, 1996

[51] Int. Cl.$^6$ .......................... A61N 1/372; A61N 1/368
[52] U.S. Cl. ...................... 607/122; 607/123; 607/9
[58] Field of Search ............... 607/4, 5, 9, 122, 607/123

[56] References Cited

U.S. PATENT DOCUMENTS

| | | | |
|---|---|---|---|
| 3,729,008 | 4/1973 | Berkovits | 607/125 |
| 3,734,095 | 5/1973 | Verrier | 604/168 |
| 3,902,501 | 9/1975 | Citron et al. | 607/126 |
| 3,903,897 | 9/1975 | Woollons et al. | 128/419 |
| 4,010,755 | 3/1977 | Preston | 128/404 |
| 4,351,345 | 9/1982 | Carney | 607/122 |
| 4,357,947 | 11/1982 | Littleford | 607/125 |
| 4,365,639 | 12/1982 | Goldreyer | 128/786 |
| 4,962,767 | 10/1990 | Brownlee | 128/786 |
| 5,127,403 | 7/1992 | Brownlee | 128/419 P |
| 5,165,403 | 11/1992 | Mehra | 607/122 |
| 5,269,326 | 12/1993 | Verrier | 607/120 |
| 5,304,139 | 4/1994 | Adams et al. | 607/122 |
| 5,312,444 | 5/1994 | Bocek et al. | 607/5 |
| 5,403,351 | 4/1995 | Saksena | 607/5 |
| 5,403,356 | 4/1995 | Hill | 607/14 |
| 5,423,772 | 6/1995 | Lurie et al. | 604/282 |
| 5,450,846 | 9/1995 | Goldreyer | 128/642 |
| 5,476,498 | 12/1995 | Ayers | 607/122 |
| 5,545,204 | 8/1996 | Cammilli et al. | 607/123 |
| 5,549,581 | 8/1996 | Lurie | 607/122 |

Primary Examiner—Marvin M. Lateef
Assistant Examiner—Carl H. Layno

[57] ABSTRACT

An atrial catheter for insertion into the coronary sinus carries free-floating sensing electrodes and one or more pacing electrodes in contact with the tissue of the coronary sinus.

7 Claims, 4 Drawing Sheets

ATRIAL PACING CATHETER AND METHOD HAVING MULTIPLE ELECTRODES IN THE RIGHT ATRIUM AND CORONARY SINUS

TECHNICAL FIELD

The present invention relates generally to medical devices adapted to be implanted in the human body and connected to catheters adapted for insertion into the heart, and more particularly to a pacemaker catheter adapted for use to prevent and treat atrial arrhythmias of the heart.

BACKGROUND ART

Atrial fibrillation, while not immediately life-threatening, can lead to serious health risks if left untreated. These health risk include the increased potential for developing a embolic stroke and for transferring the irregular atrial electrical signals to the ventricles, which can result in ventricular tachycardia and/or ventricle fibrillation. Traditionally, atrial fibrillation has been treated with antiarrhythmic drugs in an attempt to prevent or at least reduce recurrent episodes of atrial fibrillation. Prevention typically requires high systemic drug concentrations. However, chronic treatment with antiarrhythmia drugs has a high potential toxicity and even pro-arrhythmic effects.

Implantable atrial defibrillators have been proposed for the treatment atrial fibrillation. These devices rely on the discharge of electrical energy in an attempt to treat an atrial fibrillation. An example of such a device is shown in U.S. Pat. No. 5,304,139 issued to Adams et al. This patent discloses an implantable atrial defibrillator and lead configuration to be to be used in detecting and treating atrial fibrillation. However, the levels of electrical energy required to defibrillate the atrium can be quite painful for the patient.

Providing pacing electrical energy to the atria has also been suggested as a means to prevent atrial fibrillation. Pacing therapy typically requires lower levels of electrical energy than atrial defibrillators. Therefore, pacing is not typically as painful of a therapy for the patient. Examples of such devices are shown in U.S. Pat. Nos. 5,403,356, 4,357, 947 and 3,729,008. These patents disclose implantable catheters have prefixed shapes designed to engage the tissues of the right atrium. U.S. Pat. No. 5,423,772 issued to Lurie et al. discloses a fixed shape catheter for use in the coronary sinus. This catheter has a multitude of electrodes on the catheter body for providing both sensing and stimulation to the heart. Unfortunately, as the number of electrodes on the catheter body increasing, so to does the diameter of the catheter due to the proportional increase in the number of electrical leads. This increased catheter diameter also increases the catheters occlusive effect within the coronary sinus.

Consequently there is a need for catheter designs and for pacing therapies which can address the problems of atrial tachycardia.

SUMMARY DISCLOSURE OF INVENTION

The present invention provides an assembly of a pacemaker type medical device and a complimentary catheter. The device and the catheter together are used to detect and treat atrial arrhythmia and in particular to treat atrial tachycardia.

The pacemaker type device includes a housing capable of being implanted in the human body. Electrical circuits are used to analyze heart signals and to identify signals corresponding to atrial arrhythmia and for providing electrical energy to the heart through the complimentary lead system.

The catheter comprises an elongate body, and first, second, and third, electrodes on its peripheral surface connected by electrical leads extending longitudinally within the body to contact ends of the leads at a proximal end of the body. The first electrode is at a distal end of the body and the second and third electrodes are spaced longitudinally along its peripheral surface from its distal end to afford positioning the catheter in the heart with the first electrode in the coronary sinus beneath the left atrium and the second and third electrodes in the right atrium chamber or a major vein of the heart connected to the right atrium chamber. One of the electrical leads is electrically connected to the first electrode and to the third electrode, and the other electrical lead is electrically connected to the second electrode. The proximal end of the catheter is attached to the housing so that the electronic means receives signals from the heart through the first, second, and third electrodes, and the pacing electrical energy to the heart is provided through the first electrode. Thus only two leads are required to make electrical connections through which both sensing signals and pacing electrical energy to the heart are provided, resulting in a catheter body that is much smaller in diameter than if three or more electrical leads were used for those purposes. As a result, this smaller catheter diameter minimizes the occlusive effect of the catheter on the coronary sinus.

Different numbers and locations of electrodes can be used to transmit the electrical signals to the electronic means. When only first, second, and third electrodes are used, the electronic means can receive unipolar signals sensed between the first electrode and the housing to monitor activities in the left atrium chamber of the heart, and bipolar signals sensed between the second and third electrodes to monitor activities in the right atrium chamber of the heart. Preferably four electrodes are used, including a fourth electrode spaced from the first electrode to be in the coronary sinus beneath the left atrium of the heart when the first electrode is in the coronary sinus so the electronic means can receive bipolar signals sensed between the first and fourth electrodes to monitor activities in the left atrium chamber of the heart. The first electrical lead is electrically connected to the first and third electrodes, and the second electrical lead is electrically connected to the second and the fourth electrodes. The proximal end of the body is attached to the housing of the device so that the electronic means receives signals from the heart through the first, second, third, and fourth electrodes, and pacing electrical energy is provided through the first electrode or the fourth electrode. Thus, still only two leads are required to make the electrical connections which provide both the sensing from and the pacing electrical energy to the heart, and the catheter body can have the same small diameter described above.

BRIEF DESCRIPTION OF DRAWING

An illustrative embodiment of the present invention will be further described with reference to the accompanying drawing wherein like reference numerals refer to like parts in the several views, and wherein.

DETAILED DESCRIPTION OF THE INVENTION

Figure 1:
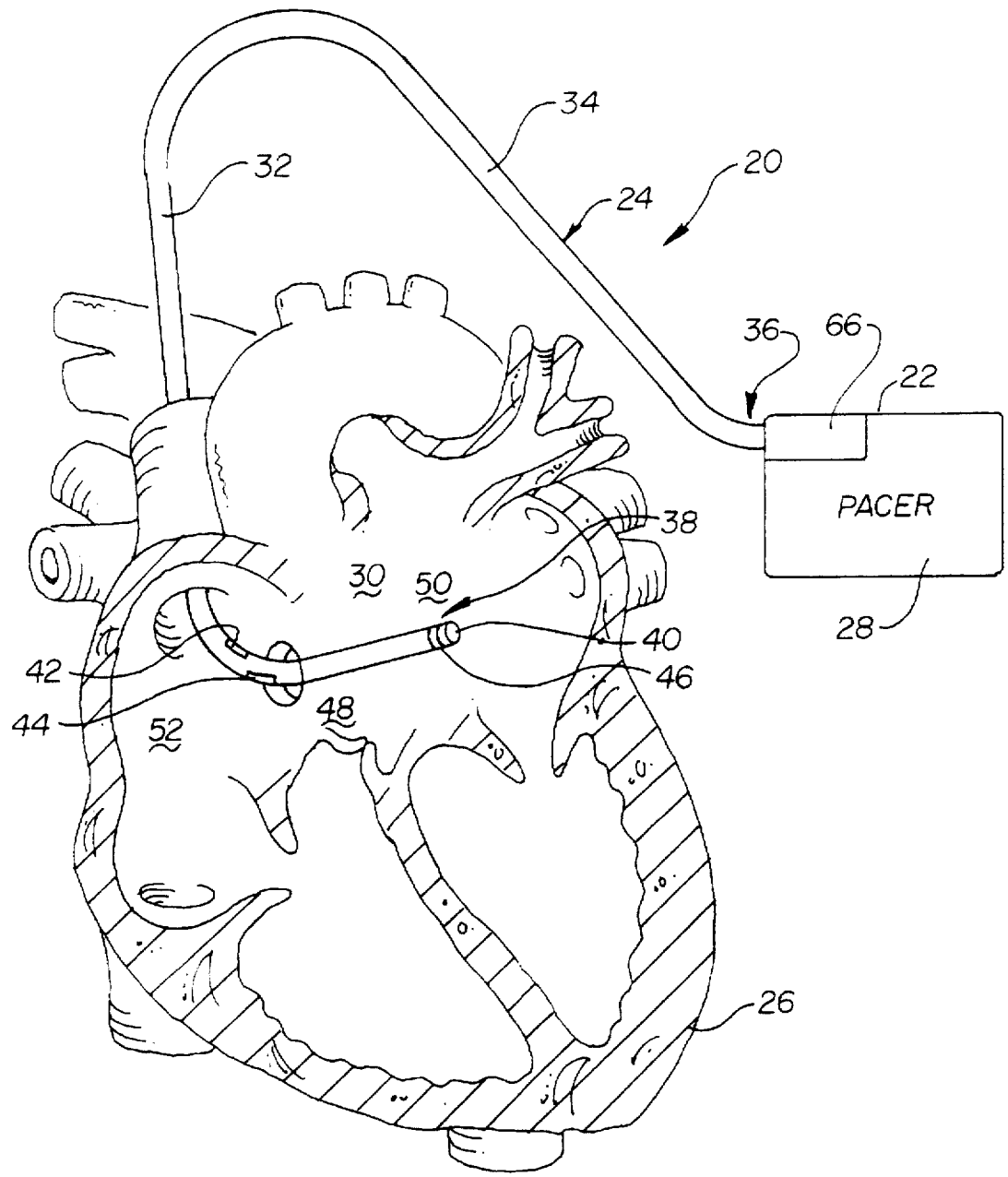
FIG. 1 is a side view of a first embodiment according to the present invention of an assembly of a medical device and catheter shown with a portion of the catheter inserted into a human heart from which portions have been removed to show details.

Referring now to FIGS. 1 through 4 of the drawing, there is shown a first embodiment of an assembly 20 of a medical device 22 and a catheter 24 according to the present invention. The assembly 20 is adapted to be implanted in a human body (not shown) with a portion of the catheter 24 inserted into a heart 26 (see FIG. 1) within the body. In use the assembly 20 will detect and analyze electric signals produced by the heart 26 and to pace the heart 26 under certain predetermined conditions.

Generally, the medical device 22 comprises a housing 28 which contains electronic means 62 (FIG. 4) including analyzing means 64 for analyzing electrical signals of the type produced by the heart 26 received through electrical connection means 66, for identifying signals indicating the onset of arrhythmia in the heart 26, and providing electrical energy to the heart 26 through the electrical connection means 66 to pace the atria 30 of the heart 26 in response to a signal from the analyzing means 64 indication a predetermined condition in the heart 26. Typically the atrial rate will be monitored and if the rate is above a physician selected level a treatable arrythmia is declared. In the method of the invention the electronic means 62 will deliver a pacing level stimulus to the atria synchronized with the monitored atrial depolarization. It is intended to deliver the pacing level energy during the refractory period of the atria.

The catheter 24 comprises an elongate body 32 having a peripheral surface 34, and proximal and distal ends 36 and 38. First, second, third, and fourth electrically conductive electrodes 40, 42, 44, and 46 adapted to receive electrical signals from the heart 26 are attached on the peripheral surface 34 of the elongated body 32. The first electrode 40 is a tip electrode at the distal end 38, whereas the second and third electrodes 42 and 44 are semi-cylindrical electrodes partially encircling and disposed on opposite sides of the peripheral surface 34 of the elongated body 32. This electrode configuration is believed to provide a larger and more discrete electrical signal from the heart 26 and is described in more detail in U.S. Pat. No. 5,127,403, the content of which patent is hereby incorporated herein by reference in its entirety. The fourth electrode 46 is annular and encircles the peripheral surface 34 of the elongated body 32.

The fourth electrode 46 is spaced longitudinally along the peripheral surface 34 from the first electrode 40 at the distal end 38 by distances in the range of 5 to 20 millimeters. The second and third electrodes 42 and 44 are spaced apart (i.e., in the range of 5 to 20 millimeters) and are spaced longitudinally along the peripheral surface 34 from the distal end 38 by distances (i.e., in the range of 11 to 16 centimeters) that afford positioning the catheter 24 in the heart 26 with the first and fourth electrodes 40 and 46 in the coronary sinus 48 beneath the left atrium 50 and the second and third electrodes 42 and 44 in the right atrium chamber 52 as is illustrated in FIG. 1. The first electrical lead 54 (FIG. 3) extends longitudinally within the elongated body 32 from a contact end (not shown) at its proximal end 36 and is electrically connected to the first and third electrodes 40 and 44. The second electrical lead 56 (FIG. 3) extends longitudinally within the elongated body 32 from a contact end (not shown) at its proximal end 36 and is electrically connected to the second and fourth electrodes 42 and 46. Alternatively, the first electrical lead 54 can be electrically connected to the first and second electrodes 40 and 42, and the second electrical lead 56 is electrically connected to the third and fourth electrodes 44 and 46.

The proximal end 36 of the catheter 24 is releasably attached to the medical device 22 with the contact ends of the electrical leads 54 and 56 (FIG.3) in electrical connection with electrical input connections 58 and 60 (FIG. 4) for the electronic means 62 so that the electronic means 62 receives bipolar P-wave signals from the right atrium chamber 52 of the heart 26 between the second and third electrodes 42 and 44 and bipolar P-wave signals from the left atrium chamber 50 of the heart 26 between the first and fourth electrodes 40 and 46. As can be seen from FIG. 4, the analyzing means 64 for analyzing electrica signals of the type produced by the heart 26 received through electrical connection means 66 can provide electrical energy to the heart 26 through the electrical connection means 66 to pace the heart 26 in response to a signal from the analyzing means 64 indicating a predetermined condition in the heart 26 in an AAT modality. The analyzing means 64 comprises a microcomputer 68 to which is coupled a program memory 70 that stores the control program that analyzes signals from the heart 26 to determine when to supply electrical energy to the heart 26 through the electrical connection means 66 to pace the heart 26, and a read/write memory 72 that is programmable to afford setting of parameters, and which stores a history of electrical impulses received from the heart 26. The microcomputer 68 is coupled to custom analog and digital circuitry 74 to which power is supplied by a depletable power supply or battery 76 and through which it is connected a telemetry antenna 78 through which information is provided to or received from the read/write memory 72. The electrical input connections 58 and 60 are connected to the custom analog and digital circuitry 74 through filters and high voltage protection circuits 80 that protect the electronic means 62 from destructive electrical inputs such as could result from defibrillation of the heart 26 by electrical impulses. A line 82 through which the electronic means can provide electrical energy to the heart 26 to pace the heart 26 is connected around the filters and high voltage protection circuits 80 between the custom analog and digital circuitry 74 and the electrical input connection 58 and through zener diode protection circuitry 86. Such electrical energy to the heart 26 paces the heart 26 in either a unipolar AAT or bipolar AAT modality.

Referring back to FIG.1, the catheter 24 is releasably attached to and can be separated from the medical device 22 to facilitate inserting it into the heart 26 of the human body. The catheter 24 is inserted into the heart 26 transvenously through a cephalic or subclavian vein (not shown) to position its distal end 38 in the coronary sinus 48 beneath the left atrium 50. The proximal end 36 of the catheter 24 is then attached to the medical device 22. The proximal end 36 of the catheter 24 and a portion of the medical device 22 are adapted to seal together to thereby engage the contact ends on the electrical leads 54 and 56 (FIG. 3) with the electrical input connections 58 and 60 (FIG. 4) of the medical device 22. The medical device 22 of the attached assembly 20 is then positioned subcutaneously within the human body.

Figure 2:
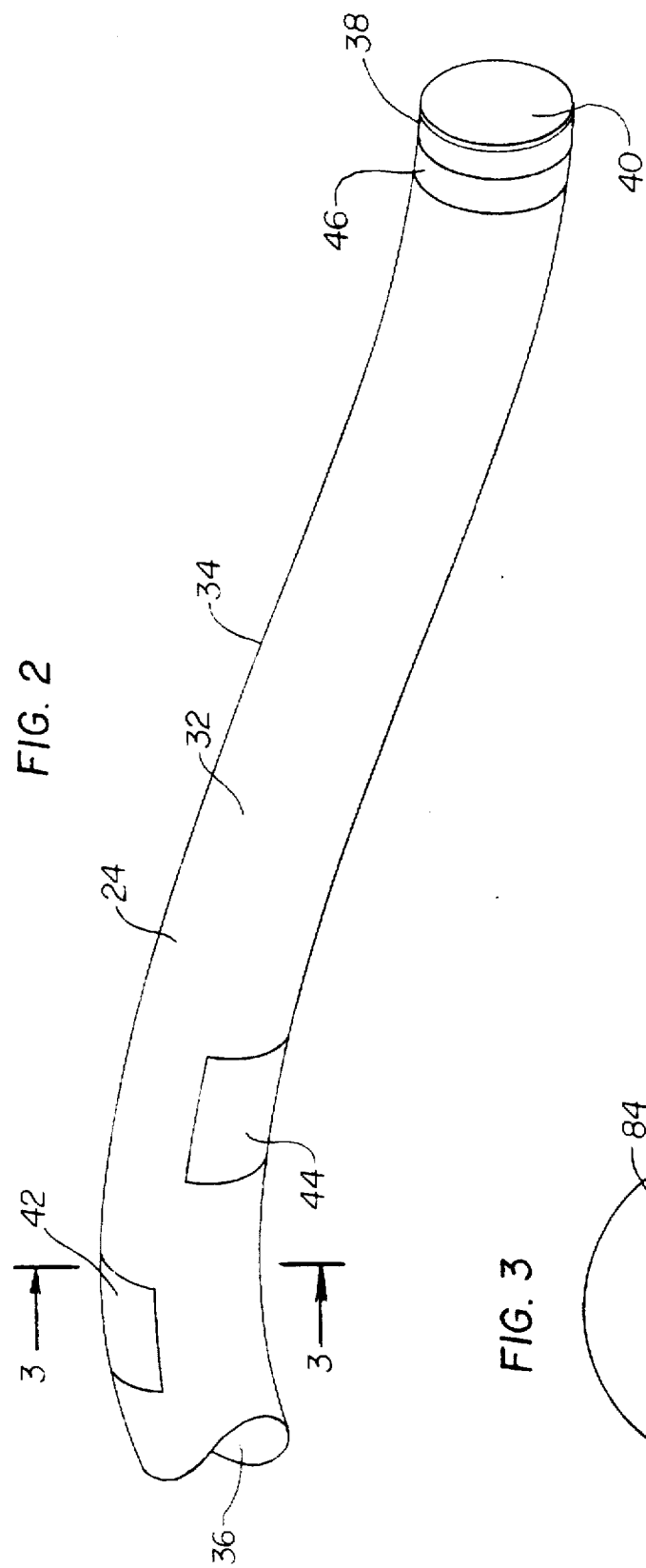
FIG. 2 is an enlarged fragmentary side view of an end portion of the catheter of FIG. 1.
Figure 3:
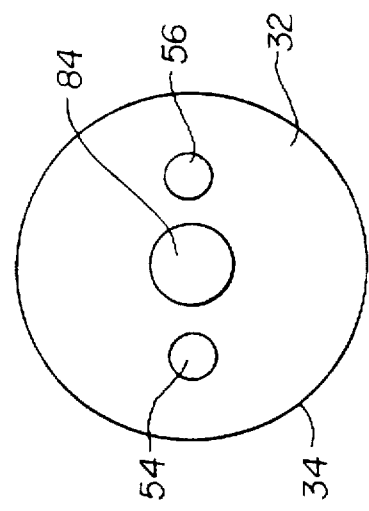
FIG. 3 is an enlarged cross sectional view taken approximately along lines 3—3 of FIG. 2.
Figure 4:
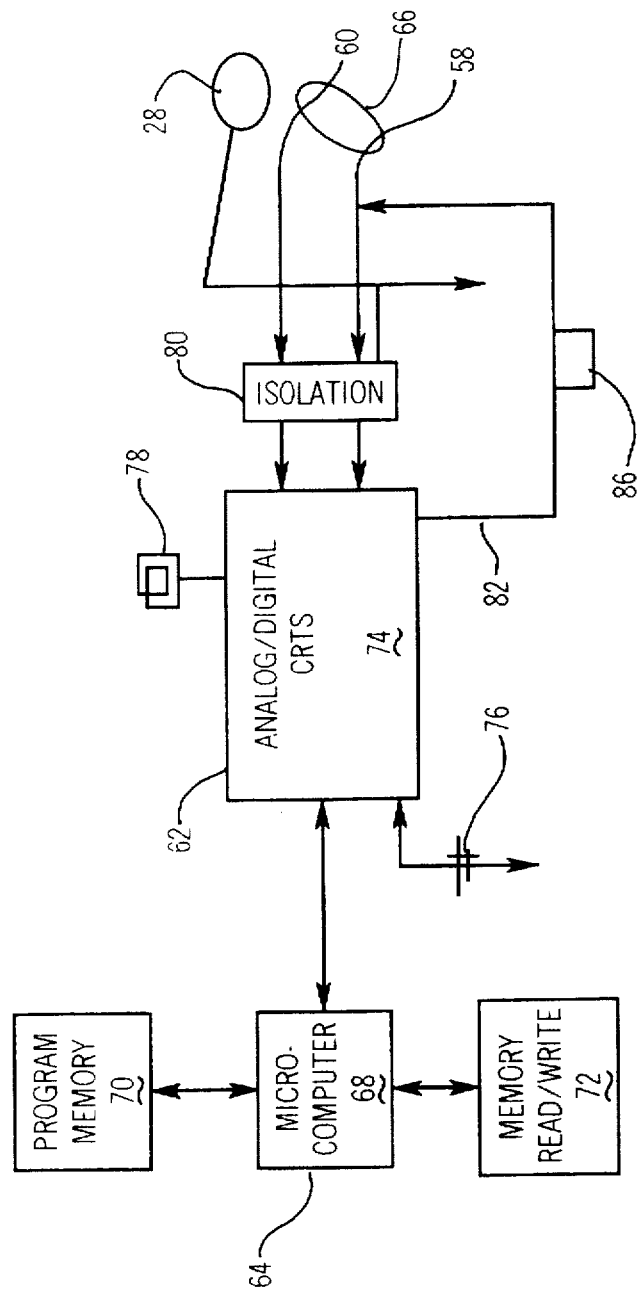
FIG. 4 is a schematic of electronic means included in the medical device of FIG. 1.

Referring now to FIG. 2, the elongated body 32 of the catheter 24 can be made by extrusion of an implantable polyurethane, silicone rubber or other implantable flexible biocompatable polymer. The length of the elongated body 32 of the catheter 24 between the proximal and distal ends 36 and 38 is preferably in the range of 55 to 100 centimeters. The electrical leads 54 and 56 (FIG. 3) can be made of MP35N alloy, or other commonly used electrical lead metal. The electrodes 40, 42, 44, and 46 can be made of implantable metal such as platinum/iridium alloys, or other commonly used electrode metal (e.g., stainless steel).

The catheter 24 has a central stylet passageway 84 extending longitudinally in the elongated body 32 from an inlet end (not shown) located at the proximal end 36 to the distal end 38. The stylet passageway 84 is adapted to receive a guide stylet for stiffening and shaping the catheter 24 during insertion of the catheter 24 into the heart 26.

Figure 5:
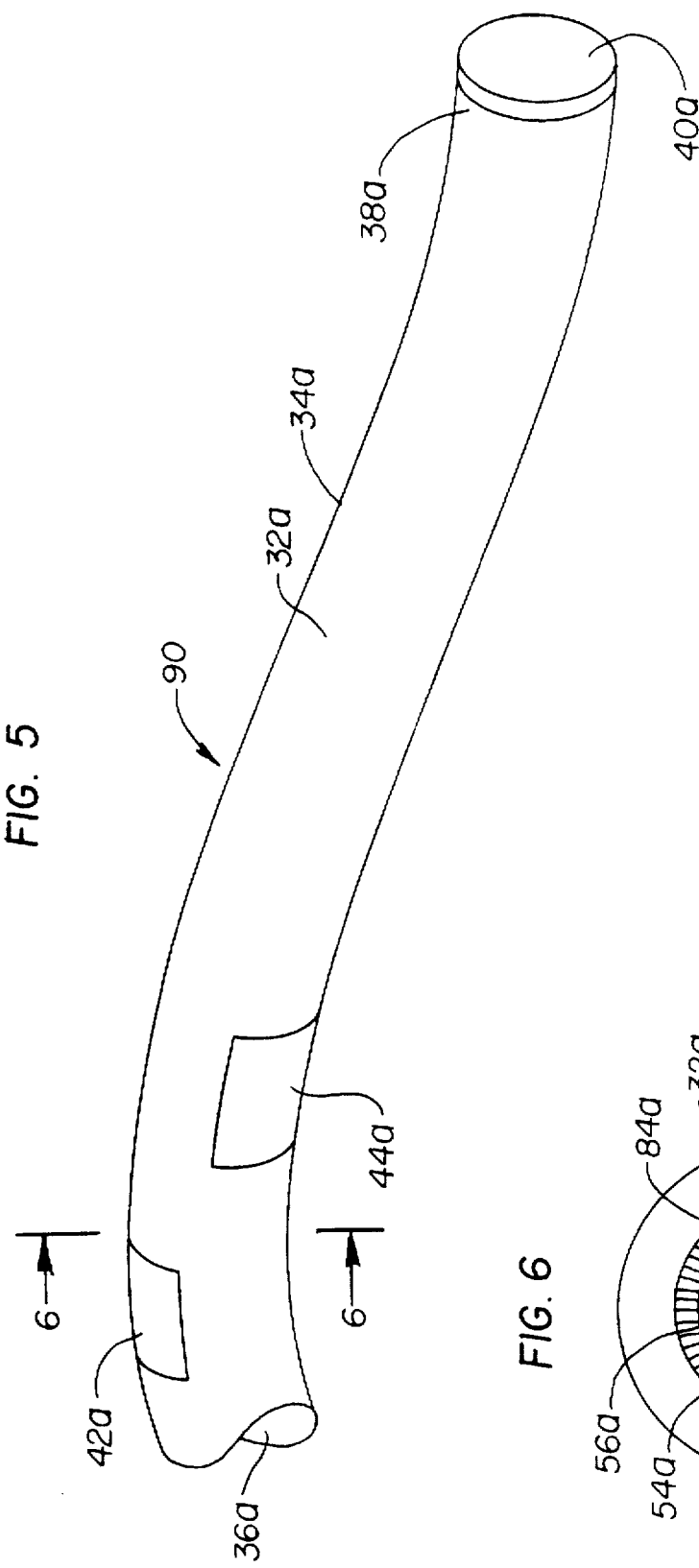
FIG. 5 is an enlarged fragmentary side view of an end portion of a second embodiment of a catheter that can be used in the assembly of FIG. 1.
Figure 6:
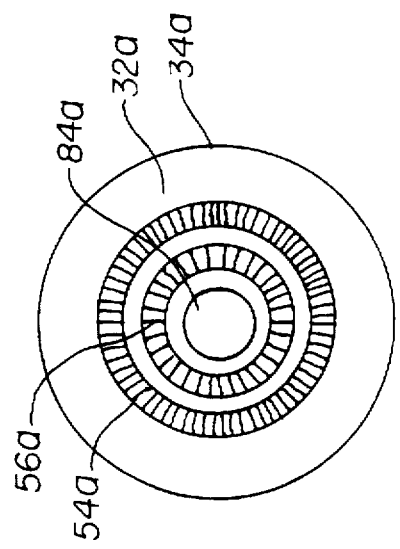
FIG. 6 is an enlarged cross sectional view taken approximately along lines 6—6 of FIG. 5.

Referring now to FIGS. 5 and 6 there is illustrated a second embodiment of a catheter 90 that can be used in an assembly with the medical device 22 described above. The catheter 90 has portions that are similar in structure to the structure described above for the catheter 24, which portions have been identified by the same reference numerals to which have been added the suffix "a".

The catheter 90 has structural features and dimensions similar to catheter 24 and functions in essentially the same manner. The catheter 90 includes an elongate body 32a having a peripheral surface 34a, and proximal and distal ends 36a and 38a. The catheter 90, however, does not include the fourth electrode 46 of the catheter 24. While leads 54a and 56a could be disposed on opposite sides of the central stylet passageway 84a in the catheter 90 as are the leads 54 and 56 in the catheter 24 (see FIG. 3), as seen in FIG. 6, in the catheter 90 the electrical leads 54a and 56a are radially spaced coaxial cylindrical sleeves constructed of braided metal and are arranged concentrically around the central stylet passageway 84a. The first electrical lead 54a extends longitudinally within the elongated body 32a from contact end (not shown) at its proximal end 36a and is electrically connected to the first and third electrodes 40a and 44a. The second electrical lead 56a extends longitudinally within the elongated body 32a from contact end (not shown) at its proximal end 36a and is electrically connected to the second electrode 42a (alternatively, the first electrical lead 54a could be electrically connected to the first and second electrodes 40a and 42a, and the second electrical lead 56a could be electrically connected to the third electrode 44a). Sensing of the left atrium 50 is unipolar between the first electrode 40a and the housing 28 of the medical device 22. Unipolar AAT pacing electrical energy can be provided to the heart 26 through the first electrode 40a.

The present invention has now been described with reference to several embodiments thereof. It will be apparent to those skilled in the art that many changes and modifications can be made in the embodiments described without departing from the scope of the present invention. For example, it is possible that the catheter designs of the present invention can be incorporated and connected to existing pacing systems, or that the apparatus of the present invention can be enslaved to existing pacing or implantable defibrillation systems. Thus the scope of the present invention should not be limited to the structures described in this application, but only by structures described by the language of the claims and the equivalents of those structures.

I claim:

1. A catheter adapted for use with a pacer said catheter comprising:

an elongate body having a peripheral surface, proximal and distal ends, first, second, and third electrodes on said peripheral surface, said first electrode being at said distal end, said second and third electrodes being spaced longitudinally along said peripheral surface from said distal end to afford positioning the catheter in the coronary sinus of the heart with said first electrode in the coronary sinus beneath the left atrium and said second and third electrodes proximate the right atrium chamber of the heart; whereby all said electrodes are located within the heart;

a first electrical lead extending longitudinally within said body from a contact end at said proximal end to said first and third electrodes, and a second electrical lead extending longitudinally within said body from a contact end at said proximal end to said second electrode.

2. A catheter according to claim 1 further including a fourth electrode on said peripheral surface, said fourth electrode being spaced longitudinally along said peripheral surface between said first electrode, and said second and third electrodes to afford positioning the catheter in the heart with said first and fourth electrodes in the coronary sinus beneath the left atrium chamber and said second and third electrodes in the right atrium chamber of the heart, said second electrical lead extending and being connected between said second and fourth electrodes; and the contact ends of said electrical leads being adapted for electrical connection with said connection means so that signals are coupled through said first and third electrodes, and said second and fourth electrodes, and the electrical energy to the heart is provided through said first electrode or said fourth electrode.

3. A catheter according to claim 1 wherein said elongate body has a stylet passageway extending longitudinally in said elongated body from an inlet end at said proximal end, said stylet passage way being adapted to receive a stylet for stiffening and shaping the catheter during insertion of the catheter.

4. A catheter according to claim 1 wherein said electrodes comprise annular shapes which encircle the peripheral surface of the body.

5. A catheter according to claim 1 wherein said electrodes are semi-annular which partially encircle the peripheral surface of the elongated body.

6. A catheter according to claim 1 wherein the length of said body between said distal and proximal ends is in the range of about 55 to 100 centimeters.

7. A method for providing sensing and pacing electrical energy to the atria of the heart for the purpose of preventing arrhythmia's of the heart, said method comprising the steps of:

providing electronic circuitry having electrical input connections for identifying electrical input signals comprising P-wave signals that indicate the electrical activity of the heart, for analyzing said electrical input signals to determine the sinus rhythm of the heart, and for producing an output signal in response to the identifying signals indicating the sinus rhythm of the heart, providing an electrical energy source and electronic controls coupled to said electronic circuitry, which electronic controls are adapted to supply pacing electrical energy from said electrical energy source synchronized with the P-wave signals upon receipt of said output signal from said analyzing means, enclosing said electronic means and source of electrical energy and electronic controls within a housing capable of being implanted in the human body.

providing a catheter, having proximal and distal ends, with at least two electrical leads with contact ends at said proximal end in electrical connection with at least three sensing electrodes adapted to receive the series of electrical signals produced by the functioning of the heart, implanting said catheter within the human body with said distal end of said catheter within the coronary sinus vein beneath the left atrium of the heart with one of said sensing electrodes located within the coronary sinus vein beneath the left atrium of the heart and two of said sensing electrodes located within the right atrium chamber of the human heart, attaching the proximal end of said catheter to the housing of the device with said contact ends of said electrical leads in electrical connection with said electrical input connections so that the electronic circuitry receives the electrical input signals through said sensing electrodes, and said pacing electrical energy to the heart is provided through said sensing electrode located within the coronary sinus beneath the left atrium, and implanting said device housing beneath the skin of the human's body so that pacing electrical energy is delivered to the left atrium chamber of the heart in synchronism with the P-wave signals of the heart.

* * * * *